(12) United States Patent
Nurmela et al.

(10) Patent No.: US 8,529,407 B2
(45) Date of Patent: Sep. 10, 2013

(54) MOBILE COMMUNICATION TERMINAL AND METHOD

(75) Inventors: Marja-Leena Nurmela, Routio (FI); Heini Tuorila, Oulu (FI); Dominick Reed, Brinkley (GB)

(73) Assignee: Nokia Corporation, Espoo (FI)

( * ) Notice: Subject to any disclaimer, the term of this patent is extended or adjusted under 35 U.S.C. 154(b) by 288 days.

(21) Appl. No.: 12/171,336

(22) Filed: Jul. 11, 2008

(65) Prior Publication Data

US 2008/0269018 A1   Oct. 30, 2008

Related U.S. Application Data

(62) Division of application No. 11/430,266, filed on May 8, 2006.

(51) Int. Cl.
*A63B 15/02* (2006.01)
*A63B 71/00* (2006.01)

(52) U.S. Cl.
USPC .................................................. 482/1; 482/8

(58) Field of Classification Search
USPC ................. 482/1–9, 901–902; 600/519–520, 600/595; 434/247; 700/91, 94; 705/2; 84/600, 84/612
IPC ................. A63B 24/00, 71/00, 15/02
See application file for complete search history.

(56) References Cited

U.S. PATENT DOCUMENTS

| | | | |
|---|---|---|---|
| 4,625,733 A | 12/1986 | Saynajakangas | |
| 4,776,323 A * | 10/1988 | Spector | ............................ 601/23 |
| 5,371,847 A | 12/1994 | Hargrove | |
| 5,486,818 A | 1/1996 | Loponen | |
| 5,491,474 A | 2/1996 | Suni et al. | |
| 5,611,346 A | 3/1997 | Heikkila et al. | |
| 5,712,995 A | 1/1998 | Cohn | |
| 5,911,145 A | 6/1999 | Arora et al. | |
| 6,008,809 A | 12/1999 | Brooks | |
| 6,013,007 A | 1/2000 | Root et al. | |
| 6,021,351 A | 2/2000 | Kadhiresan et al. | |
| 6,199,021 B1 | 3/2001 | Cote et al. | |
| 6,229,454 B1 | 5/2001 | Heikkila et al. | |
| 6,272,365 B1 | 8/2001 | Ronkainen et al. | |

(Continued)

FOREIGN PATENT DOCUMENTS

CN         1384330        12/2002
CN      1384330 (A)      12/2002

(Continued)

OTHER PUBLICATIONS http://dictionary.reference.com/browse/calendar, definition of calendar.*

(Continued)

*Primary Examiner* — Oren Ginsberg
(74) *Attorney, Agent, or Firm* — Alston & Bird LLP (57) ABSTRACT

A method in a mobile communication device includes detecting an input indicating a planned pattern of intensity of an exercise session in at least one timed step, storing a music inventory of songs including a rhythm associated with each song in a memory of the mobile communication device, selecting a playlist of songs with rhythms correlated to each of the at least one timed step of the planned pattern of intensity, and playing the playlist in response to initiation of the exercise session.

26 Claims, 5 Drawing Sheets

| 885 ID | 886 Song name | 887 BPM | 888 ... |
|---|---|---|---|
| 889 | High speed chase | 150 | ... |
| 890 | Chilling | 106 | ... |
| 891 | Keep it cool | 112 | ... |
| 892 | Kicking it | 132 | ... |
| 893 | Evereasy | 102 | ... |

(56) References Cited

U.S. PATENT DOCUMENTS

| | | |
|---|---|---|
| 6,277,080 B1 | 8/2001 | Nissila et al. |
| 6,327,486 B1 | 12/2001 | Nissila et al. |
| 6,356,848 B1 | 3/2002 | Cote et al. |
| 6,361,502 B1 | 3/2002 | Puoloakanaho et al. |
| 6,477,397 B1 | 11/2002 | Ronkainen et al. |
| 6,537,227 B2 | 3/2003 | Kinnunen et al. |
| 6,645,126 B1 | 11/2003 | Martin et al. |
| 6,716,139 B1* | 4/2004 | Hosseinzadeh-Dolkhani et al. .................. 482/1 |
| 6,808,473 B2* | 10/2004 | Hisano et al. .................. 482/8 |
| 6,854,628 B1 | 2/2005 | Stehr |
| 7,149,982 B1 | 12/2006 | Duperrouzel et al. |
| 7,156,773 B2 | 1/2007 | Takai et al. |
| 7,177,672 B2* | 2/2007 | Nissila ................ 600/519 |
| 7,220,220 B2 | 5/2007 | Stubbs et al. |
| 7,287,232 B2 | 10/2007 | Tsuchimura et al. |
| 2002/0142887 A1 | 10/2002 | O'Malley |
| 2004/0008224 A1 | 1/2004 | Molander et al. |
| 2004/0046637 A1 | 3/2004 | Wesby Van Swaay |
| 2004/0117212 A1 | 6/2004 | Kong et al. |
| 2004/0122297 A1 | 6/2004 | Stahmann et al. |
| 2005/0107216 A1 | 5/2005 | Lee et al. |
| 2005/0124463 A1* | 6/2005 | Yeo et al. .................. 482/8 |
| 2005/0197063 A1 | 9/2005 | White |
| 2005/0202934 A1 | 9/2005 | Olrik et al. |
| 2005/0228244 A1 | 10/2005 | Banet |
| 2007/0016875 A1 | 1/2007 | Santos-Gomez |
| 2007/0027000 A1* | 2/2007 | Shirai et al. .................. 482/8 |
| 2007/0049461 A1* | 3/2007 | Kim et al. .................. 482/8 |
| 2007/0060446 A1* | 3/2007 | Asukai et al. .................. 482/8 |
| 2007/0169614 A1* | 7/2007 | Sasaki et al. .................. 84/612 |
| 2007/0213178 A1 | 9/2007 | Lemmela et al. |
| 2007/0249467 A1* | 10/2007 | Hong et al. .................. 482/1 |
| 2008/0096726 A1* | 4/2008 | Riley et al. .................. 482/8 |
| 2008/0153671 A1* | 6/2008 | Ogg et al. .................. 482/3 |
| 2008/0188354 A1* | 8/2008 | Pauws et al. .................. 482/8 |
| 2008/0254946 A1* | 10/2008 | Pauws et al. .................. 482/8 |

FOREIGN PATENT DOCUMENTS

| | | |
|---|---|---|
| DE | 3439238 | 5/1985 |
| DE | 4215549 | 11/1992 |
| DE | 69414362 | 6/1999 |
| DE | 29910633 | 9/1999 |
| DE | 20008882 | 7/2000 |
| DE | 20 2005 00901 U1 | 9/2005 |
| DE | 202005009016 | 10/2005 |
| EP | 0665947 | 8/1995 |
| EP | 836165 | 4/1998 |
| FI | 68734 | 10/1985 |
| FI | 88223 | 12/1992 |
| FI | 88972 | 1/1993 |
| FI | 96380 | 2/1995 |
| FI | 4069 | 7/1997 |
| FI | 961148 | 12/1997 |
| FI | 100924 | 3/1998 |
| FI | 4150 | 9/1999 |
| FI | 981436 | 12/1999 |
| FI | 20010311 | 8/2002 |
| FR | 2676848 | 11/1992 |
| FR | 2681493 | 3/1993 |
| FR | 2793672 | 11/2000 |
| GB | 2137363 | 3/1984 |
| GB | 2 137 363 A | 10/1984 |
| GB | 2149514 | 6/1985 |
| GB | 2257523 | 1/1993 |
| GB | 2258587 | 2/1993 |
| GB | 2326240 | 12/1998 |
| GB | 2339833 | 2/2000 |
| HK | 812/1989 | 10/1989 |
| HK | 113/1996 | 1/1996 |
| HK | 306/1996 | 3/1996 |
| JP | 10-063265 | 3/1998 |
| JP | 2001-203783 A | 7/2001 |
| JP | 2002-190007 | 7/2002 |
| JP | 2003-175139 | 6/2003 |
| JP | 2003-323503 A | 11/2003 |
| JP | 2005-134201 | 5/2005 |
| JP | 2006-072865 A | 3/2006 |
| KR | 10-2005-0027589 A | 3/2005 |
| KR | 20050110507 | 11/2005 |
| SG | 9591671-4 | 5/1991 |
| SG | 9592117-7 | 7/1991 |
| WO | 95/05578 | 2/1995 |
| WO | WO 02/067449 A1 | 8/2002 |
| WO | 02/071935 A1 | 9/2002 |
| WO | 03/099114 A1 | 12/2003 |
| WO | 2004016173 A1 | 2/2004 |
| WO | WO 2005/096597 A1 | 10/2005 |

OTHER PUBLICATIONS http://dictionary.reference.com/browse/calendar, definition of calendar, Jan. 6, 2011, Note: This NPL was attached to the non-final office action dated Jan. 31, 2011. It is being re-cited since the PTO-892 included with the Jan. 31, 2011 office action did not include a date for this NPL.*

Chinese Office Action dated Apr. 23, 2010.

Korean Office Action dated Aug. 26, 2010.

Japanese Office Action dated Mar. 8, 2011.

Australian Search Report and Written Opinion for Application No. SG 200807661-4, mailed Oct. 2, 2009.

Hungarian Search Report for Application No. 2008076614A, completed Apr. 2, 2010.

Hungarian Search Report for Application No. 2008076614, mailed Apr. 15, 2010.

Office Action for Russian Application No. 2008146257/12, mailed Mar. 24, 2010.

Office Action for Japanese Application No. 2009-508519 dated Mar. 13, 2012.

* cited by examiner

| 885 ID | 886 Song name | 887 BPM | 888 ... |
|---|---|---|---|
| 889 | High speed chase | 150 | ... |
| 890 | Chilling | 106 | ... |
| 891 | Keep it cool | 112 | ... |
| 892 | Kicking it | 132 | ... |
| 893 | Evereasy | 102 | ... |

Fig 8

MOBILE COMMUNICATION TERMINAL AND METHOD

CROSS-REFERENCE TO RELATED APPLICATIONS

This application is a divisional of, claims priority from, and the benefit of U.S. application Ser. No. 11/430,266 filed on May 8, 2006, status pending, the disclosure of which is incorporated herein by reference in its entirety.

FIELD

The aspects of the disclosed embodiments generally relate to mobile terminals and more particularly exercise applications of mobile terminals.

BACKGROUND

Mobile terminals, or mobile (cellular) telephones, for mobile telecommunications systems like GSM, UMTS, D-AMPS and CDMA2000 have been used for many years now. In the older days, mobile terminals were used almost exclusively for voice communication with other mobile terminals or stationary telephones. More recently, the use of modern terminals has been broadened to include not just voice communication, but also various other services and applications such as www/wap browsing, video telephony, electronic messaging (e.g. SMS, MMS, email, instant messaging), digital image or video recording, FM radio, music playback, exercise analysis, electronic games, calendar/organizer/time planner, word processing, etc. Furthermore, the modern terminals have local connectivity abilities, such as Bluetooth, allowing the mobile terminals to communicate with a wide array of devices.

One relatively new use of mobile terminals is to use them as exercise tracking devices. The terminal is then able to measure and record time and distance during exercise. However, users sometimes lack motivation to actually follow through and perform the exercise as originally intended.

It is generally desired to provide improvements to the user interface and functionality and both internal and external interoperability of mobile terminals used for exercise tracking.

SUMMARY OF THE DISCLOSED EMBODIMENTS

In view of the above, an advantage of the disclosed embodiments is to solve or at least reduce the problems discussed above.

A first expression of a first inventive aspect is a method for providing a user interface of an exercise application of a mobile communication terminal comprising a display, the method comprising: accepting a first input defining a user layout of containers for exercise related measurements; accepting a second input for associating an exercise related measurement with each of the containers; and when exercising is determined to have begun, displaying the user layout of the containers on the display, each container showing an associated exercise related measurement.

The method may furthermore comprise: when a switch view user input is detected, displaying a second layout.

The second layout may differ from the user layout.

Each of the exercise related measurements may be measurements selected from a group comprising distance, time, burnt calories, speed, steps, step intensity, minutes per mile, minutes per kilometer, distance graph, speed graph, and intensity graph.

The method may furthermore comprise, before accepting a first input defining a user layout: presenting layout alternatives of available user layouts on the display.

A second expression of the first inventive aspect is a mobile communication terminal configured to provide a user interface of an exercise application, the mobile communication terminal comprising: means for accepting a first input defining a user layout of containers for exercise related measurements; means for accepting a second input for associating an exercise related measurement with each of the containers; and means for, when exercising is determined to have begun, displaying the user layout of the containers on the display, each container showing an associated exercise related measurement.

A third expression of the first inventive aspect is a mobile communication terminal configured to provide a user interface of an exercise application, the mobile communication terminal comprising a display, a keypad and a controller, the controller being configured to accept a first input defining a user layout of containers for exercise related measurements; the controller being configured to accept a second input for associating an exercise related measurement with each of the containers; and the controller being configured to, when exercising is determined to have begun, display the user layout of the containers on the display, each container showing an associated exercise related measurement.

A fourth expression of the first inventive aspect is a computer program product comprising software instructions that, when executed in a mobile communication terminal, performs the method according to the first expression of the first inventive aspect.

A first expression of a second inventive aspect is a method for accepting input from an external device to a mobile communication terminal, the external device being usable to an exercise application of the mobile communication terminal, the method comprising: detecting a presence of the device; setting up a communication channel between the device and the mobile communication terminal; when data becomes available in the device, making the data available to the exercise application.

The device may be a device comprising an actuator, the data comprising user input data being generated when the actuator is actuated.

The device may be configured to fit on a motorcycle, the method furthermore comprising: the exercise application using the user input data to determine a time for a lap.

The device may be a device comprising a movement sensitive sensor, the data comprising movement data being generated when the movement sensitive sensor detects movement.

The device may be configured to fit on a bicycle, the method furthermore comprising: the exercise application using the movement data to determine a roughness of a track followed by the bicycle.

The device may be configured to fit on a skateboard, the method furthermore comprising: the exercise application using the movement data to determine a skill level of a rider of the skateboard.

The device may be a device comprising an global positioning system receiver, the data comprising positional data being generated using the global positioning receiver.

The device may configured to fit on a bicycle, the method furthermore comprising: the exercise application using the positional data to determine a measurement selected from the group comprising speed and position.

A second expression of the second inventive aspect is a mobile communication terminal configured to accept input from an external device, the external device being usable to an exercise application of the mobile communication terminal, the mobile communication terminal comprising: means for detecting a presence of the device; means for setting up a communication channel between the device and the mobile communication terminal; means for, when data becomes available in the device, making the data available to the exercise application.

A third expression of the second inventive aspect is a mobile communication terminal configured to accept input from an external device, the external device being usable to an exercise application of the mobile communication terminal, the mobile communication terminal comprising a display, a keypad and a controller, the controller being configured to detect a presence of the device; the controller being configured to set up a communication channel between the device and the mobile communication terminal; the controller being configured to, when data becomes available in the device, make the data available to the exercise application.

A fourth expression of the second inventive aspect is a system used during exercise, the system comprising: an external data providing device, comprising means for capturing data; and means for transmitting the data to a receiving device; the system furthermore comprising: a mobile communication terminal configured to accept input from the external data providing device, the external device being usable to an exercise application of the mobile communication terminal, the mobile communication terminal comprising: means for detecting a presence of the device; means for setting up a communication channel between the device and the mobile communication terminal; means for, when data becomes available in the device, making the data available to the exercise application.

A fifth expression of the second inventive aspect is a computer program product comprising software instructions that, when executed in a mobile communication terminal, performs the method according to the first expression of the second inventive aspect.

A first expression of a third inventive aspect is a method for adding a planned exercise entry in an exercise schedule in a mobile communication terminal, the method comprising: receiving user input for a planned start time for the planned exercise entry; receiving user input for a planned exercise type of the planned exercise entry; determining a music playlist to be associated with the planned exercise entry; and when an exercise associated with the planned exercise entry is determined to have started, playing the playlist.

The determining a music playlist may involve determining a playlist based on the exercise type.

The determining a music playlist may involve: determining at least one exercise period being at least a subset of a planned exercise associated with the planned exercise entry, each of the at least one exercise periods having an associated exercise period intensity; for each of the at least one exercise periods, determining a range of beats per minute matching the intensity; for each of the at least one exercise periods, presenting at least one song, the song being available to the mobile communication terminal, the song having a beats per minute measurement matching the range of beats per minute; and for each of the at least one exercise periods, receiving user input to select one of the at least one song, to be comprised in the playlist.

The determining a music playlist may involve: determining at least one exercise period being at least a subset of a planned exercise associated with the planned exercise entry, each of the at least one exercise periods having an associated exercise period intensity; for each of the at least one exercise periods, determining a range of beats per minute matching the intensity; for each of the at least one exercise periods, determining one song being available to the mobile communication terminal, the song having a beats per minute measurement matching the range of beats per minute, the song to be comprised in the playlist.

A second expression of the third inventive aspect is a mobile communication terminal capable of adding a planned exercise entry in an exercise schedule in the mobile communication terminal comprising: means for receiving user input for a planned start time for the planned exercise entry; means for receiving user input for a planned exercise type of the planned exercise entry; means for determining a music playlist to be associated with the planned exercise entry; and means for, when an exercise associated with the planned exercise entry is determined to have started, playing the playlist.

A third expression of the third inventive aspect is a mobile communication terminal capable of adding a planned exercise entry in an exercise schedule in the mobile communication terminal comprising a display, a keypad and a controller, the controller being configured to receive user input for a planned start time for the planned exercise entry; the controller being configured to receive user input for a planned exercise type of the planned exercise entry; the controller being configured to determine a music playlist to be associated with the planned exercise entry; and the controller being configured to, when an exercise associated with the planned exercise entry is determined to have started, play the playlist.

A fourth expression of the third inventive aspect is a computer program product comprising software instructions that, when executed in a mobile communication terminal, performs the method according to the first expression of the third inventive aspect.

Other objectives, features and advantages of the disclosed embodiments will appear from the following detailed disclosure, from the attached dependent claims as well as from the drawings.

Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of the element, device, component, means, step, etc., unless explicitly stated otherwise. The steps of any method disclosed herein do not have to be performed in the exact order disclosed, unless explicitly stated.

BRIEF DESCRIPTION OF THE DRAWINGS

Embodiments of the present invention will now be described in more detail, reference being made to the enclosed drawings, in which:

FIG. 2b is a schematic side view illustrating the mobile terminal in FIG. 2a.

FIGS. 5a-d are schematic diagrams showing how the user can affect the layout of an exercise application in the mobile terminal of FIG. 2a.

FIG. 7 is a schematic diagram illustrating the relationship between beats per minute and exercise intensity in the mobile terminal of FIG. 2a.

FIG. 8 is a schematic diagram illustrating a table containing data related to songs available to the mobile terminal of FIG. 2a.

DETAILED DESCRIPTION OF THE DISCLOSED EMBODIMENTS

The aspects of the disclosed embodiments will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout.

Figure 1:
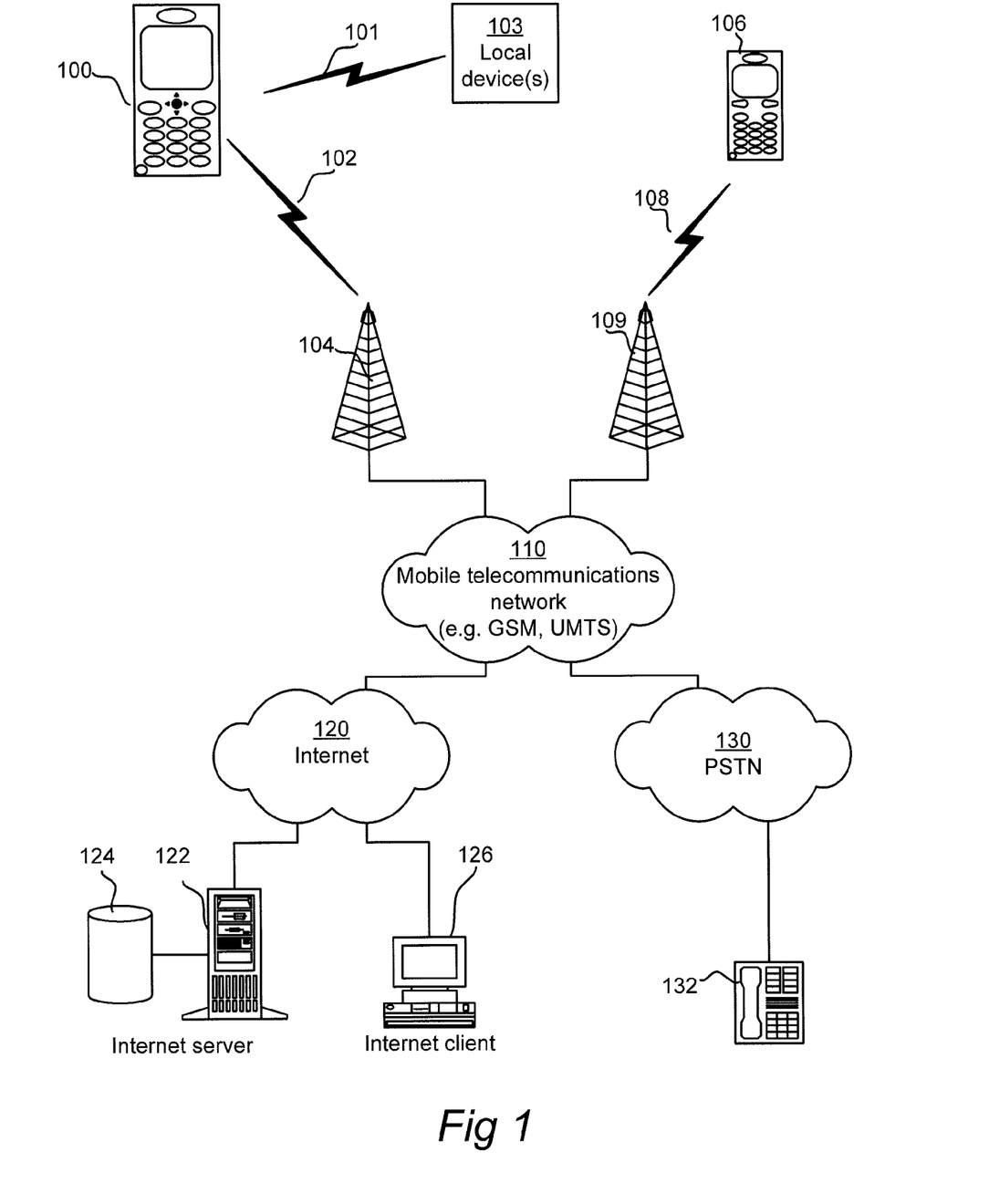
FIG. 1 is a schematic illustration of a cellular telecommunication system, as an example of an environment in which the present invention may be applied.

FIG. 1 illustrates an example of a cellular telecommunications system in which the invention may be applied. In the telecommunication system of FIG. 1, various telecommunications services such as cellular voice calls, www/wap browsing, cellular video calls, data calls, facsimile transmissions, music transmissions, still image transmissions, video transmissions, electronic message transmissions and electronic commerce may be performed between a mobile terminal 100 according to the present invention and other devices, such as another mobile terminal 106 or a stationary telephone 132. It is to be noted that for different embodiments of the mobile terminal 100 and in different situations, different ones of the telecommunications services referred to above may or may not be available; the invention is not limited to any particular set of services in this respect.

The mobile terminals 100, 106 are connected to a mobile telecommunications network 110 through RF links 102, 108 via base stations 104, 109. The mobile telecommunications network 110 may be in compliance with any commercially available mobile telecommunications standard, such as GSM, UMTS, D-AMPS, CDMA2000, FOMA and TD-SCDMA.

The mobile telecommunications network 110 is operatively connected to a wide area network 120, which may be Internet or a part thereof. An Internet server 122 has a data storage 124 and is connected to the wide area network 120, as is an Internet client computer 126. The server 122 may host a www/wap server capable of serving www/wap content to the mobile terminal 100.

A public switched telephone network (PSTN) 130 is connected to the mobile telecommunications network 110 in a familiar manner. Various telephone terminals, including the stationary telephone 132, are connected to the PSTN 130.

The mobile terminal 100 is also capable of communicating locally via a local link 101 to one or more local devices 103. The local link can be any type of link with a limited range, such as Bluetooth, a Universal Serial Bus (USB) link, a Wireless Universal Serial Bus (WUSB) link, an IEEE 802.11 wireless local area network link, an RS-232 serial link, etc. The local devices 103 can for example be various sensors that can communicate measurement values to the mobile terminal 100 over the local link 101.

Figure 2A:
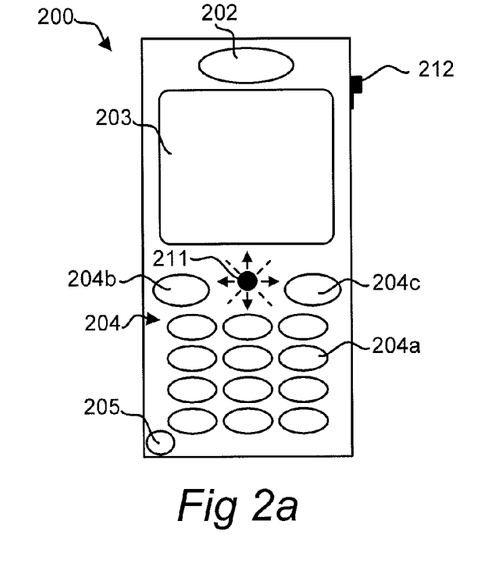
FIG. 2a is a schematic front view illustrating a mobile terminal according to an embodiment of the present invention.

An embodiment 200 of the mobile terminal 100 is illustrated in more detail in FIG. 2a. The mobile terminal 200 comprises a speaker or earphone 202, a microphone 205, a display 203 and a set of keys 204 which may include a keypad 204a of common ITU-T type (alpha-numerical keypad representing characters "0"-"9", "*" and "#") and certain other keys such as soft keys 204b, 204c and a joystick 211 or other type of navigational input device.

Figure 2B:
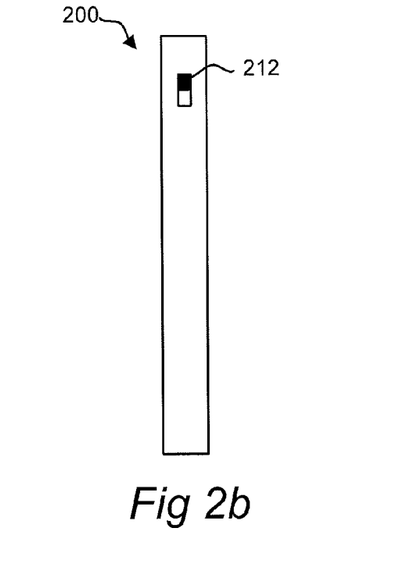

A mode switch button 212 is also provided, as can be seen more clearly in FIG. 2b. The button is used to switch an operating mode of the mobile terminal. In this embodiment, the button is by default positioned in an upper position. When the user wants to switch modes, the button is moved to a lower position and released, after which the button returns to the default upper position by mechanical means, such as a spring or similar. As the man skilled in the art will realize, the functionality of the mode switch button could easily be replaced with a push button or any other suitable type of input device.

Figure 3:
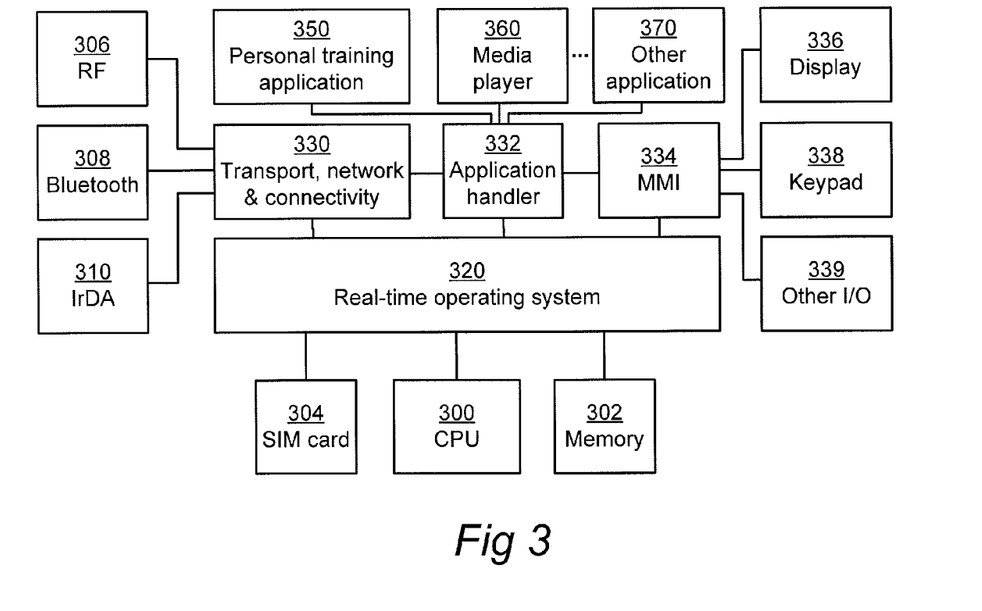
FIG. 3 is a schematic block diagram representing an internal component, software and protocol structure of the mobile terminal shown in FIGS. 2a and 2b.

The internal component, software and protocol structure of the mobile terminal 200 will now be described with reference to FIG. 3. The mobile terminal has a controller 300 which is responsible for the overall operation of the mobile terminal and is preferably implemented by any commercially available CPU ("Central Processing Unit"), DSP ("Digital Signal Processor") or any other electronic programmable logic device. The controller 300 has associated electronic memory 302 such as RAM memory, ROM memory, EEPROM memory, flash memory, or any combination thereof. The memory 302 is used for various purposes by the controller 300, one of them being for storing data and program instructions for various software in the mobile terminal. The software includes a real-time operating system 320, drivers for a man-machine interface (MMI) 334, an application handler 332 as well as various applications. The applications can include a personal exercise application 350, a media player application 360, as well as various other applications 370, such as applications for voice calling, video calling, sending and receiving SMS, MMS or email, web browsing, an instant messaging application, a phone book application, a calendar application, a control panel application, a camera application, one or more video games, a notepad application, etc.

The MMI 334 also includes one or more hardware controllers, which together with the MMI drivers cooperate with the display 336/203, keypad 338/204 as well as various other I/O devices such as microphone, speaker, vibrator, ringtone generator, LED indicator, etc. As is commonly known, the user may operate the mobile terminal through the man-machine interface thus formed.

The software also includes various modules, protocol stacks, drivers, etc., which are commonly designated as 330 and which provide communication services (such as transport, network and connectivity) for an RF interface 306, and optionally a Bluetooth interface 308 and/or an IrDA interface 310 for local connectivity. The RF interface 306 comprises an internal or external antenna as well as appropriate radio circuitry for establishing and maintaining a wireless link to a base station (e.g. the link 102 and base station 104 in FIG. 1). As is well known to a man skilled in the art, the radio circuitry comprises a series of analogue and digital electronic components, together forming a radio receiver and transmitter.

These components include, i.a., band pass filters, amplifiers, mixers, local oscillators, low pass filters, AD/DA converters, etc.

The mobile terminal also has a SIM card 304 and an associated reader. As is commonly known, the SIM card 304 comprises a processor as well as local work and data memory.

Figure 4:
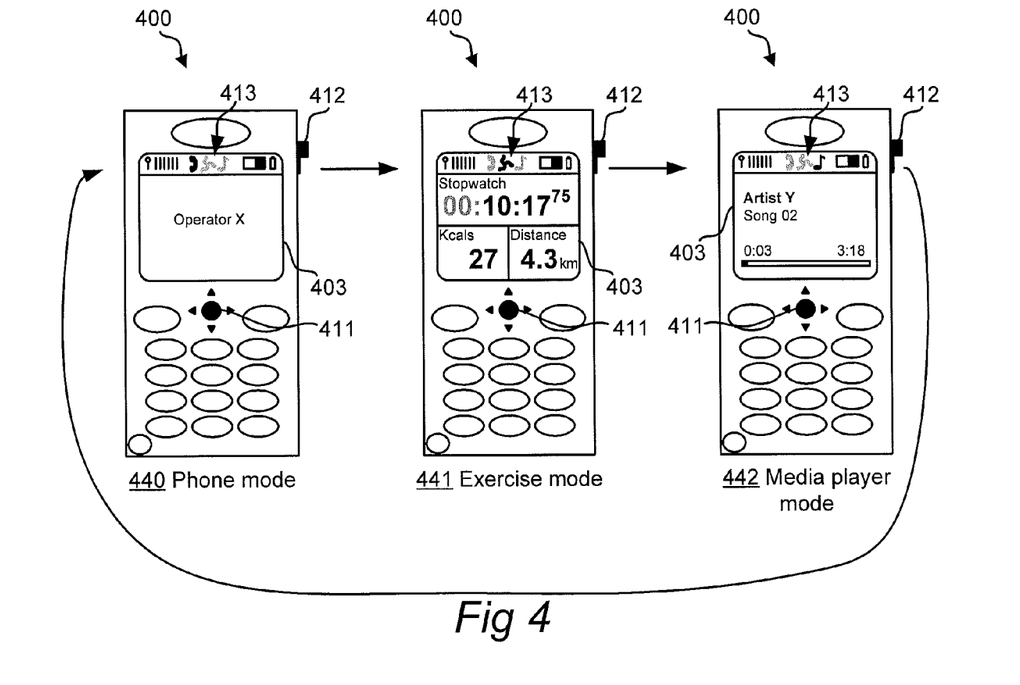
FIG. 4 is a schematic diagram showing how operational modes can be switched in an embodiment of the present invention.

FIG. 4 shows how operational modes can be switched in an embodiment of the present invention. The mobile terminal 400, such as mobile terminal 200 of FIG. 2*a*, comprises a display 403, such as display 203 of FIG. 2*a*, a joystick 411, such as joystick 211 of FIG. 2*a*, and a mode switch button 412 such as mode switch button 212 of FIG. 2*a* to allow the user to switch operational modes.

Operational modes are modes where the mobile terminal 400 behaves in a specific way. For example, FIG. 4 shows 3 operational modes: a phone mode 440, an exercise mode 441 and a media player mode 442.

When the mobile terminal 400 is in the phone mode 440, the mobile terminal behaves as a user would expect a regular mobile terminal to behave. In other words, a menu system and/or shortcuts allow the user to instruct the mobile terminal to perform a desired function, such as voice telephony, www/wap browsing, video telephony, electronic messaging (e.g. SMS, MMS, email, instant messaging), digital image or video recording, electronic games, calendar/organizer/time planner, word processing, etc.

When the mobile terminal 400 is in the exercise mode 441, the main purpose of the mobile terminal is to provide the user with applications related to the physical exercise of the user. The mobile terminal can in this mode support exercising such as running, cycling, etc.

In one embodiment, an accelerometer is integrated in the mobile terminal 400. In another embodiment, an external accelerometer is connected to the mobile terminal 400, e.g. over a local link, such as the local link 101 in FIG. 1. The accelerometer can detect acceleration and thereby steps that the user takes while the mobile terminal is carried by the user. When an accelerometer is integrated or connected to the mobile terminal 400, the mobile terminal automatically measures movement during the day. If the user previously has entered personal information, such as weight, height, etc., the mobile terminal 400 can convert the data from the accelerometer to other measurements, such as covered distance and burnt calories. Optionally, a GPS (Global Positioning System) receiver can be either integrated in, or connected to, the mobile terminal 400 to allow accurate distance measurement. Also, an external heart beat monitor can be connected to the mobile terminal 400 to detect heart beats and calculate heart rate.

When the mobile terminal 400 is in the media player mode 442, the main purpose of the mobile terminal is to play media to the user. For example, the media player can play music or sound files, such as MP3 (mpeg-1 audio layer 3) files, AAC (advanced audio coding) files or ogg files. Optionally, the media player can also be used to listen to FM (frequency modulated) radio, or to play video files according to standards such as MPEG-2, MPEG-4 or H.323.

As the user switches operational modes with mode switch button 412, the modes are switched serially. In the illustrated embodiment, there is a list of operational modes consisting of the phone mode 440, the exercise mode 441, and the media player mode 442, in that order. Consequently, if the mobile terminal 400 is in the phone mode 440 and the user actuates the mode switch button 412, the phone switches to the exercise mode 441. Similarly, if the mobile terminal 400 is in the exercise mode 441 and the user actuates the mode switch button 412, the phone switches to the media player mode 442.

Finally, if the mobile terminal 400 is in the media player mode 443 and the user actuates the mode switch button 412, the phone loops back and switches to the phone mode 440.

To allow the user to easily determine what mode is currently used, elements of the user interface are specific for each mode. There are a multitude of distinguishing user interface elements that can vary to allow the user to see what mode is currently active, e.g., a centrally located light by the joystick 411 can change color, the background on the display 403 can have different colors or appearances, or the entire theme of the user interface with colors and fonts can change. In one embodiment, one of a set of icons at the top of the display 403 is highlighted to indicate which mode is active.

Mode changes can also change sound effects. For example in phone mode 440, the sounds may be discrete or even absent for actions such as button press, enter menu, exit menu, while in exercise mode 441, distinct and loud sounds are played for these actions to give clear feedback to the user while exercising. The media player mode 441 may have a totally different, more cool or ambient sound scheme on the actions mentioned in order to give feedback to the user on actions performed, while still not excessively disturbing the experience of listening to music. Optionally, the sound scheme can furthermore vary depending on whether headphones are connected to the mobile terminal 400 or not. The changes of sounds does not need to be totally different sounds; the changes could be effects applied to sounds. For example, a sound for a button press in phone mode could be reused in the media player mode, with a strong reverberation effect on it to give a more ambient effect while still providing familiarity to the user.

Additionally, a temporary user indication can be given when the actual mode change occurs. For example, the vibrator may vibrate on a mode change, where the vibration is either always identical for all modes or every mode has a particular vibration associated with it. Additionally, a dialog can show the name of the new operational mode in the display 403, or a sound effect or speech synthesizer pronouncing the new mode can be played to the user.

It is to be noted that although the modes can be switched certain appropriate processing of an inactive mode can still be performed. For example, the exercise application can count the steps of the user in the background, regardless of what mode the mobile terminal is in. Similarly, the media player can let the user hear an FM radio station while the mobile terminal is in exercise mode, or the phone application can temporarily interrupt current processing if there an incoming phone call is detected.

FIGS. 5*a-d* are schematic diagrams showing how the user can affect the layout of an exercise application in the mobile terminal of FIG. 2*a*. The mobile terminal has previously been set to be in exercise mode.

Figure 5A:
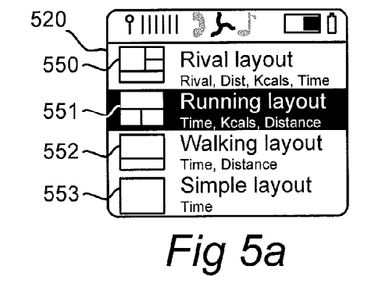

When a user indicates, for example through an options menu, that the user desires to change the default layout of the exercise screen, a view such as a view 520 of FIG. 5*a* is displayed on the display. Here the user has the ability to select a layout corresponding to his/her preference. In the view 520, in this example, there are four menu items available, each corresponding to a layout. The menu item 550 corresponds to a layout with the name "Rival layout", having the default measurements of rival time, distance, kcal and time. The menu item 551 corresponds to a layout with the name "Running layout", having the default measurements of time, kcal and distance. The menu item 552 corresponds to a layout with the name "Walking layout", having the default measurements of time and distance. Finally in this example, the menu item 553 corresponds to a layout with the name "Simple layout", having the default measurement of time. Alternatively, the layout is automatically chosen depending on what training program the user has chosen, e.g. race rival, running, walking, etc.

Figure 5B:
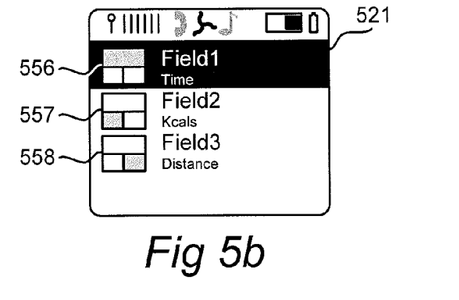

Once the layout is selected, the user can edit the exercise related measurements that are to be displayed. For example, if the user selects the running layout of FIG. 5a, and indicates that the exercise measurements are to be modified, a view such as view 521 of FIG. 5b is shown. Here there are three menu items, one menu item 556 for the top container, one menu item 557 for the bottom left container and one menu item 558 for the bottom right container. The number of menu items correspond to the number of containers, or fields, for the layout in question. A container is simply a space of the layout that can be used to show a measurement. Each container has a default measurement already assigned to it, but the user has the ability to change what measurement should be displayed in each container. Examples of measurements that the user can select are: distance, time, burnt calories, speed, steps, step intensity, minutes per mile, minutes per kilometer, distance graph, speed graph, and intensity graph.

Figure 5C:
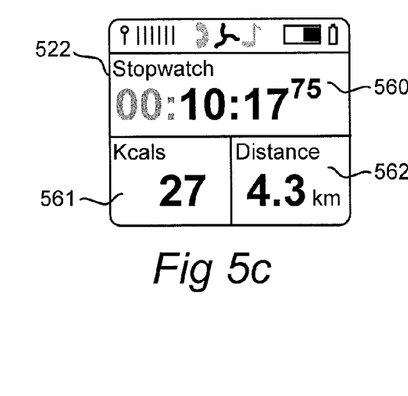

Once the user starts to exercise, a view like view 522 of FIG. 5c is shown. Corresponding to the view 521 of FIG. 5b, the top container 560 shows time, the bottom left container 561 shows a number of burnt kcal, and the bottom right shows a distance from the start of the exercise.

Figure 5D:
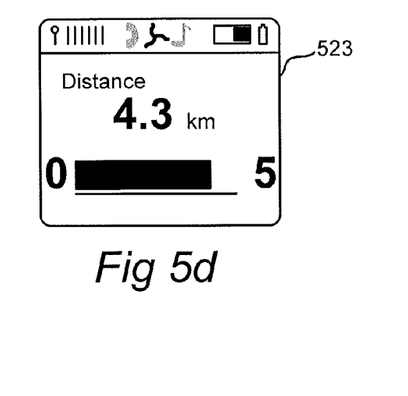

While the view 521 of FIG. 5c has been configured to be the default view, the user can also switch to other views as needed during exercise. For example, the user could tap on the screen, which is detected by a motion sensor in the mobile terminal, effecting a switch of the view on the mobile phone. Alternatively, the user can press a button or speak a voice command to switch views. For example, a second view can be the view 523 which is shown in FIG. 5d. Here the user can see both text and graphics representing the distance. The graphics shows how far has been covered of the current track. Additional views could be shown on the display by the user by effecting the same user input again. Preferably, there is a circular list of layouts.

The mobile terminal can be configured to have two or more user definable layouts or additional layouts after the default layout could be determined by the mobile terminal. For example, the additional layouts could depend on what training program is used, or what time of the day or week it is.

Figure 6:
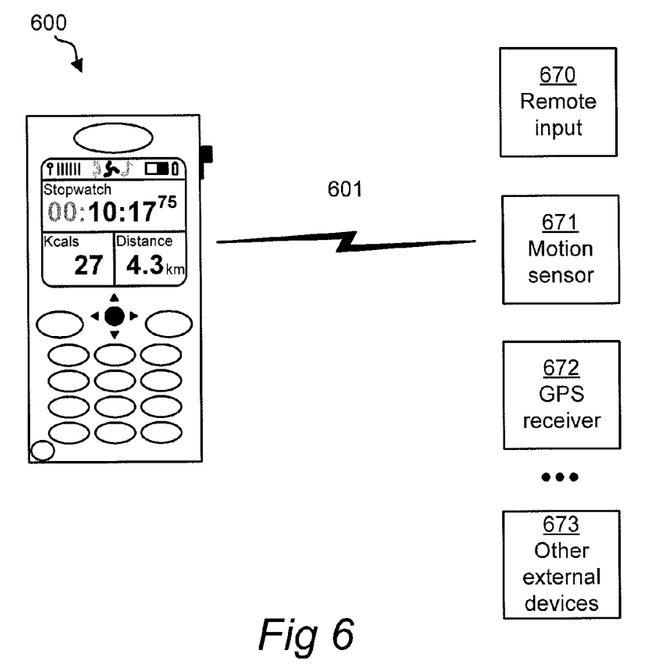
FIG. 6 is a schematic diagram illustrating communication between the mobile terminal of FIG. 2a with external devices.

FIG. 6 is a schematic diagram illustrating communication between the mobile terminal of FIG. 2a and external devices 670-673. The communication takes place over a local link 601, such as local link 101 of FIG. 1.

In order to provide communication between the mobile terminal and an external device, a connection process proceeds as follows. First the mobile terminal detects a presence of an external device. This may occur through the mobile terminal polling for devices or the device itself may initiate communication. Subsequently, a communication channel is set up between the external device and the mobile terminal. Once the communication channel is set up, bidirectional communication is available.

The external devices may for example be a remote input device 670, a motion sensor device 671, a GPS receiver 672 on any other suitable external devices 673.

The remote input device is a device with for example one or more buttons on it. The device can be mounted in a place which is convenient for the user, whereby the input on the remote device can be used for a suitable action by the exercise application in the mobile terminal. For example, the remote input device could be mounted on a steering wheel of a motorcycle, close to a finger a thumb, allowing the user to press a button whenever the user passes a specific point of a track, such as a finish line. By using a collection of the times of such presses to the button on the remote input device, the exercise application can calculate lap times, which the user can analyze after he or she has finished riding the motorcycle. Alternatively or additionally, the exercise application can read out lap times when they become available using a voice synthesizer to a headset that the user can wear.

If a motion sensor, such as an accelerometer, is not provided in the mobile terminal itself, an external motion sensor 671 can be connected to the mobile terminal. The motion sensor 671 is then used for all uses described above where a motion sensor is suitable. Alternatively or additionally, the motion sensor can be mounted on a bicycle such as a mountain bike. The motion data collected by the exercise application can then be used to determine a roughness of a track that the bike follows. The roughness can be measured over time and the user can be presented with a graph giving an attractive overview of the roughness of a track. The vertical axis of such a graph typically indicates roughness and the horizontal axis is typically time or distance.

Another use of an external motion sensor is for skateboarding. If the motion sensor is mounted on a skateboard, the motion data can be used by the exercise application to determine the skill level of the user. Typically, if the user is a beginner, the motions are erratic and wobbly. For intermediate users, the motions are smoother, while for advanced users, the motions are more active, but in a controlled manner, indicating that the user is performing various tricks.

If a GPS receiver 672 is connected to the mobile terminal, data about position can be fed to the exercise application, and also for other applications of the mobile terminal. The GPS can also provide accurate speed and time measurements. This is particularly useful for exercises like bicycle riding or even rowing, assuming that the mobile terminal and the GPS receiver are water resistant. The exercise application can then receive data about speed and distance which is difficult in other ways for these sports, such as using a motion sensor. Also when running, although a motion sensor can give a decent indication of speed and distance, the GPS receiver gives a much more accurate measurement.

Any other external device 673 that are considered suitable can also be connected over the local link 601.

Figure 7:
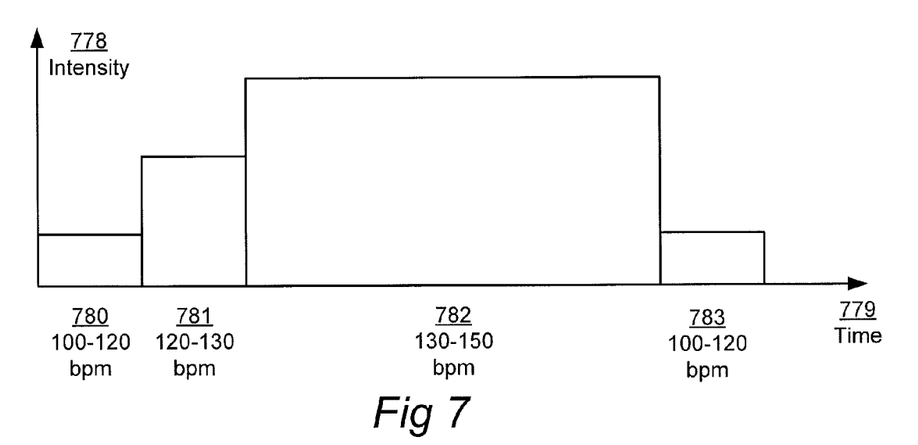

FIG. 7 is a schematic diagram illustrating the relationship between beats per minute and exercise intensity in the mobile terminal of FIG. 2a.

In the exercise application, it is provided access to a calendar allowing the user to plan his/her exercise schedule. This helps the user to reach a more general goal, such as to lose 10 pounds, or to exercise 3 hours a week. The user can consequently add exercise entries to the calendar and inputs essential parameters such as planned start time. The user can also indicate what exercise type should be associated with the entry. The exercise type affects the exercise intensity over time, and could for example be an interval training exercise, full intensity, nice and easy, or regular program. In FIG. 7, an example is shown illustrating a regular program. On the vertical axis, intensity 778 is indicated and on the horizontal axis, time 779 is indicated.

In a first time period 780, or exercise period, intensity is relatively low. Therefore, an associated beats per minute (bpm) for this period is also relatively low, in this case 100-120 bpm. As is described below, an associated song would have a bpm measurement of 100-120 bpm. This is the warm-up period of the exercise.

In a second time period 781, intensity is higher than in the first period 780. Therefore, an associated beats per minute (bpm) for this period is also higher, in this case 120-130 bpm.

As is described below, an associated song would have a bpm measurement of 120-130 bpm. This is a ramp-up period of the exercise, where intensity is increasing.

In a third, longer, time period 782, intensity is even higher than in the second period 781. Therefore, an associated beats per minute (bpm) for this period is also even higher, in this case 130-150 bpm. As is described below, an associated song would have a bpm measurement of 130-150 bpm. This is the bulk time of the exercise in this example, where the user is performing, e.g. running, at a relatively high speed.

In a fourth time period 783, intensity is again at a relatively low level, like the first period 780. Therefore, an associated beats per minute (bpm) for this period is also relatively low, in this case 100-120 bpm. As is described below, an associated song would have a bpm measurement of 100-120 bpm. This is a cool-down period of the exercise, where intensity is decreasing before the exercise ends.

Other exercise types would have other arrangements of time periods with their respective intensities. Although these other exercise types are not illustrated here, any type of exercise type can be associated with beats per minute and any type of exercise type is thus within the scope of the current invention.

Figure 8:
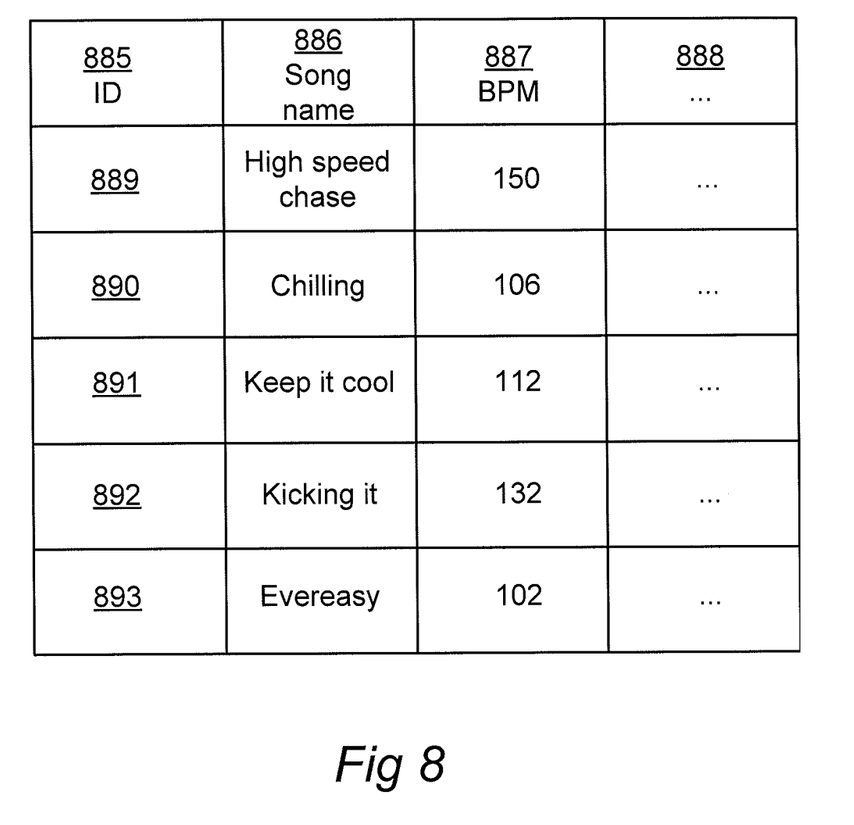

FIG. 8 is a schematic diagram illustrating a table containing data related to songs available to the mobile terminal of FIG. 2a.

The table has headings ID 885, giving each table entry in the table an identity, song name 886, bpm 887, as well as other headings 888, such as artist, album, genre, composer, year of recording, track number, star rating, etc.

This exemplary table contains five table entries 889-893. These table entries can be considered in conjunction with the exercise type of FIG. 7 and the bpm range for each time period. The first time period 780 and the fourth time period 783 have a bpm range that fits with table entries 890, 891 and 893. The second time period 781 has a bpm range that fits with table entry 892 and the third time period 782 has a bpm range that fits with table entry 889.

With the relationship between the exercise type for the calendar entry selected, a playlist containing songs matching the exercise type can thus be created. When there are several songs to choose from for a specific time period, the user can select a song manually, or the mobile terminal can select what song or songs are to be played. The mobile terminal can select songs using any appropriate selection criteria, such as songs that are played the most are selected first, songs are selected randomly, etc. If the song or songs that are determined to correspond to a time period have a combined duration that is longer than the duration for the time period, the song or songs are truncated in the playlist in order to match the set time period. Alternatively, the time period is adjusted to fit in duration with the song or songs for that time period.

A playlist matching an exercise type for a calendar entry in the exercise calendar is thus created.

The invention has mainly been described above with reference to a few embodiments. However, as is readily appreciated by a person skilled in the art, other embodiments than the ones disclosed above are equally possible within the scope of the invention, as defined by the appended patent claims.

What is claimed is:

1. A method in a device comprising:
    accessing an electronic calendar application stored in the device;
    storing a planned exercise entry in the electronic calendar, the planned exercise entry including a day, a start time and a duration;
    associating an exercise schedule with the planned exercise entry, the exercise schedule comprising an exercise type, the exercise type including at least one timed step, the at least one timed step having a planned pattern of intensity and a target heart rate range for an exercise type;
    storing a music playlist to be associated with each timed step of the planned exercise entry in a memory of the device, the music playlist including one or more songs associated with each of the timed steps, wherein each song of the music playlist associated with a timed step has a tempo corresponding to the target heart rate range for the timed step;
    accessing an exercise application in the device;
    identifying from the calendar application the planned exercise entry corresponding to a current date and time;
    determining that an exercise associated with the planned exercise entry corresponding to the current date and time has started and;
    playing a song from the playlist that corresponds to the exercise associated with the planned exercise entry corresponding to the current date and time.

2. The method according to claim 1, comprising selecting a playlist of songs based on a predetermined exercise type.

3. The method according to claim 1, wherein selecting a playlist of songs involves:
    determining at least one exercise period being at least a subset of a planned exercise associated with a planned exercise session, each of said at least one exercise periods having an associated exercise period intensity;
    for each of said at least one exercise periods, determining a range of beats per minute matching said intensity;
    for each of said at least one exercise periods, presenting at least one song from an inventory of songs, said song having a beats per minute measurement matching said range of beats per minute; and
    for each of said at least one exercise periods, detecting an input to select one of said at least one song, to be comprised in said playlist.

4. The method according to claim 1 wherein the memory is part of a media player and the exercise schedule is performed on said media player.

5. The method according to claim 1, further comprising:
    for each of said at least one timed step of said exercise session, determining a range of beats per minute matching said intensity;
    for each of said at least one timed step of said exercise session, selecting one of said songs having a rhythm matching said range of beats per minute, said song or songs to be comprised in said playlist.

6. The method of claim 1 comprising:
    a first timed step in the exercise schedule where the target heart range is a low intensity, and the tempo of each song associated with the first timed step has a beat per minute corresponding to the low intensity target heart rate range;
    a second timed step following the first timed step, the second timed step having an intensity higher than the low intensity of the first timed step, and wherein the tempo of each song of the second timed step has a beat per minute corresponding to the a target heart rate range of the second timed step;
    a third timed step, the third timed step having a duration that is longer than each of the first and second timed steps, and an intensity of the third timed step is higher than each of the first and second timed steps, wherein the tempo of each song of the third timed step has a beat per minute corresponding to the a target heart rate range of the third timed step; and a fourth timed step, the fourth timed step having an intensity that is substantially equal to or less than the intensity of the first timed step and the tempo of each song of the fourth timed step has a beat per minute corresponding to the a target heart rate range of the fourth timed step, a duration of the fourth timed step being less than the duration of the third timed step.

7. The method of claim 6, wherein a song to be played during each of the timed steps is automatically selected from the music playlist, wherein when more than one song is available for a timed step, a song that is most played is automatically selected to be played first.

8. The method of claim 7, wherein when a duration of a selected song is less than a duration of the timed step, a second song is automatically selected to be played during the timed step.

9. The method of claim 7, wherein when a duration of a selected song is greater than a duration of the timed step, the selected song is truncated to match the duration of the timed step.

10. The method of claim 7, wherein when a duration of the selected song does not match a duration of the timed step, the duration of the timed step is automatically adjusted to match the duration of the selected song.

11. The method of claim 6, wherein the planned exercise entry in the calendar comprises an exercise schedule that includes an exercise type for each of the first, second, third and fourth timed steps, and wherein a song corresponding to the exercise type and intensity for each of the first, second, third and fourth timed step is automatically selected from the playlist for each of the first, second, third and fourth timed step.

12. An apparatus comprising:
at least one processor; and
at least one memory including computer program code, the at least one memory and the computer program code configured to, with the at least one processor, cause the apparatus at least to:
access an electronic calendar application stored in a device;
store a planned exercise entry in the electronic calendar, the planned exercise entry including a day, a start time and a duration;
associate an exercise schedule with the planned exercise entry, the exercise schedule comprising- an exercise type, the exercise type including at least one timed step, the at least one timed step having a planned pattern of intensity and a target heart range for an exercise type;
store a music playlist to be associated with each timed step of the planned exercise entry in a memory of the device, the music playlist including one or more songs associated with each of the timed steps, wherein each song of the music playlist associated with a timed step has a tempo corresponding to the target heart range for the timed step;
access an exercise application in the device;
identify from the calendar application the planned exercise entry corresponding to a current date and time;
determine that an exercise associated with the planned exercise entry corresponding to the current date and time has started; and
play a song from the playlist that corresponds to the exercise associated with the planned exercise entry corresponding to the current date and time.

13. The apparatus according to claim 12, wherein the apparatus comprises a media player.

14. The apparatus according to claim 12, wherein the apparatus comprises a mobile communication terminal.

15. The apparatus of claim 12, wherein the at least one timed step comprises a first timed step in the exercise schedule where the target heart range is a low intensity, and the tempo of each song associated with the first timed step has a beat per minute corresponding to the low intensity target heart rate range, a second timed step following the first timed step, the second timed step having an intensity higher than the low intensity of the first timed step, and wherein the tempo of each song of the second timed step has a beat per minute corresponding to the target heart rate range of the second timed step, a third timed step, the third timed step having a duration that is longer than each of the first and second timed steps, and an intensity of the third timed step is higher than each of the first and second timed steps, wherein the tempo of each song of the third timed step has a beat per minute corresponding to the target heart rate range of the third timed step, and a fourth timed step, the fourth timed step having an intensity that is substantially equal to or less than the intensity of the first timed step and the tempo of each song of the fourth timed step has a beat per minute corresponding to the target heart rate range of the fourth timed step, a duration of the fourth timed step being less than the duration of the third timed step.

16. The apparatus of claim 12, wherein if a duration of a selected song associated with the timed step does not match a duration of the timed step, the duration of the timed step is automatically adjusted to match the duration of the selected song.

17. A computer program product comprising:
at least one computer readable non-transitory memory medium having program code stored thereon, the program code which when executed by an apparatus causes the apparatus at least to:
access an electronic calendar application stored in the device;
store a planned exercise entry in the electronic calendar, the planned exercise entry including a day, a start time and a duration;
associate an exercise schedule with the planned exercise entry, the exercise schedule comprising an exercise type, the exercise type including at least one timed step, the at least one timed step having a planned pattern of intensity and a target heart rate range for an exercise type;
store a music playlist to be associated with each timed step of the planned exercise entry in a memory of the device, the music playlist including one or more songs associated with each of the timed steps, wherein each song of the music playlist associated with a timed step has a tempo corresponding to the target heart rate range for the timed step;
access an exercise application in the device;
identify from the calendar application the planned exercise entry corresponding to a current date and time;
determine that an exercise associated with the planned exercise entry corresponding to the current date and time has started; and
play a song from the playlist that corresponds to the exercise associated with the planned exercise entry corresponding to the current date and time.

18. A mobile communication terminal comprising:
a display;
a keypad; and
a controller;

wherein said controller is configured to:
 store in an electronic calendar application a planned exercise entry for an exercise schedule according to a date, a start time and a duration,
 associate an exercise type with the exercise schedule, the exercise type including at least one timed step, each timed step having a planned pattern of intensity and a target heart range for an exercise associated with the timed step;
 store a music inventory of songs in a memory; and
 wherein said controller is further adapted to allow the user to associate a playlist of songs for each timed step, wherein each song in the playlist of songs has a tempo with a beat that corresponds to the target heart rate range of the planned pattern of intensity for the timed step; and
 wherein said controller is further adapted to play said playlist in response to an initiation of the planned exercise entry by accessing an exercise application, identifying a planned exercise entry in the calendar application corresponding to a current date and time, determining a start of an exercise type, determining a current timed step for the exercise type and the planned pattern of intensity for the current timed step and selecting a song from the playlist that corresponds to the planned pattern of intensity of the current timed step.

19. The mobile communication terminal of claim 18, wherein the at least one timed step comprises a first timed step in the exercise schedule where the target heart range is a low intensity, and the tempo of each song associated with the first timed step has a beat per minute corresponding to the low intensity target heart rate range, a second timed step following the first timed step, the second timed step having an intensity higher than the low intensity of the first timed step, and wherein the tempo of each song of the second timed step has a beat per minute corresponding to the target heart rate range of the second timed step, a third timed step, the third timed step having a duration that is longer than each of the first and second timed steps, and an intensity of the third timed step is higher than each of the first and second timed steps, wherein the tempo of each song of the third timed step has a beat per minute corresponding to the target heart rate range of the third timed step, and a fourth timed step, the fourth timed step having an intensity that is substantially equal to or less than the intensity of the first timed step and the tempo of each song of the fourth timed step has a beat per minute corresponding to the target heart rate range of the fourth timed step, a duration of the fourth timed step being less than the duration of the third timed step.

20. The mobile communication terminal of claim 18, wherein if a duration of a selected song in the playlist of songs associated with a timed step does not match a duration of the timed step, the duration of the timed step is automatically adjusted to match the duration of the selected song.

21. A method comprising:
 receiving user input for a planned start time for a planned exercise entry in an exercise schedule in a mobile communication terminal;
 receiving user input for a planned exercise type of said planned exercise entry;
 determining a music playlist to be associated with said planned exercise entry, said determining a music playlist involves determining a playlist based on said exercise type; and
 when an exercise associated with said planned exercise entry is determined to have started, playing said playlist.

22. The method according to claim 21, wherein said exercise type is one taken from a group comprising cycling, running and walking.

23. The method according to claim 21, wherein receiving user input for a planned start time for said planned exercise entry comprises adding an exercise entry to a calendar.

24. The method according to claim 21, wherein the planned exercise entry includes a day and a duration.

25. A non-transitory computer-readable storage medium encoded with instructions that, when performed by a processor, cause performance of:
 receiving user input for a planned start time for a planned exercise entry in an exercise schedule in a mobile communication terminal;
 receiving user input for a planned exercise type of said planned exercise entry;
 determining a music playlist to be associated with said planned exercise entry, said determining a music playlist involves determining a playlist based on said exercise type; and
 when an exercise associated with said planned exercise entry is determined to have started, playing said playlist.

26. The non-transitory computer-readable storage medium of claim 25, wherein receiving user input for a planned start time for said planned exercise entry comprises adding an exercise entry to a calendar.

* * * * *